United States Patent [19]

Strickler

[11] Patent Number: 4,482,713

[45] Date of Patent: Nov. 13, 1984

[54] QUATERNARY AMMONIUM SALTS AND THEIR PREPARATION

[75] Inventor: Rainer Strickler, Heidelberg, Fed. Rep. of Germany

[73] Assignee: BASF Aktiengesellschaft, Fed. Rep. of Germany

[21] Appl. No.: 394,183

[22] Filed: Jul. 1, 1982

[30] Foreign Application Priority Data

Jul. 4, 1981 [DE] Fed. Rep. of Germany ....... 3126522

[51] Int. Cl.$^3$ ............................................. C07D 295/08
[52] U.S. Cl. ....................................... 544/177; 546/248; 546/236; 546/240; 548/574; 564/292; 564/293; 564/294; 260/459 A
[58] Field of Search ................ 544/177; 564/292, 293, 564/294; 546/248, 240, 236; 548/574; 260/459 A

[56] References Cited

U.S. PATENT DOCUMENTS 2,049,463 8/1936 Major et al. .......................... 260/25
2,103,272 12/1937 Roeder ................................... 260/25
3,448,134 6/1969 McGraw ............................... 260/448

OTHER PUBLICATIONS

Babaian et al., *Journal of General Chemistry of the USSR*, vol. 28, (1958), pp. 1314–1317; vol. 25, (1955), pp. 1567–1570.
Sidgwick, *The Organic Chemistry of Nitrogen*, (1956), p. 28.
Morrison et al., *Organic Chemistry*, 2nd ed., (1970), p. 748.
Weber et al., *Phase Transfer Catalysis in Organic Synthesis*, (1977), p. 73.
Chem. Abstracts, vol. 31, No. 4, Feb. 20, 1937, col. 1102, No. 5, Columbus, Ohio.
J. Pharmacol. 58, 140–154, (1936), Hunt et al., "Ethers of Choline and Allied Compounds".

*Primary Examiner*—Robert W. Ramsuer
*Attorney, Agent, or Firm*—Keil & Weinkauf

[57] ABSTRACT

Novel quaternary ammonium salts of the general formula

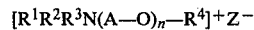

$$[R^1R^2R^3N(A-O)_n-R^4]^+Z^-$$

where $R^1$ and $R^2$ are identical or different and each is alkyl, aryl, aralkyl, alkylaryl, alkoxyalkyl, or a (poly)alkylene glycol radical, or $R^1$ and $R^2$, together with the nitrogen atom, are a heterocyclic ring, or one or more substituents $R^1$ or $R^2$ are polyfunctional so that the salt contains not less than 2 ammonium groups, $R^3$ and $R^4$ are identical or different monovalent radicals of one or more alkylating agents $R^3X$ or $R^4X$, for example an (ar)alk(en)yl halide, sulfate or methosulfate or an (alkyl)aryl-sulfonate or -sulfonic acid ester, A is alkylene of 2 to 10 carbon atoms, n is an integer and Z is either X or another salt-forming anion or a hydroxyl ion, are prepared by N-alkylation and O-alkylation of an alkanolamine with the aid of a phase transfer catalyst and are useful as cationic surfactants, etc.

4 Claims, No Drawings

QUATERNARY AMMONIUM SALTS AND THEIR PREPARATION

Among cationic surfactants, quaternary ammonium salts have achieved great importance, and are used, for example, as biocides, as cationic detergents, as emulsifiers in building protection and anti-corrosion technology and in ore dressing, and as dyeing assistants in the textile and leather industries.

The starting materials for quaternary ammonium salts are tertiary amines, which can be converted into the ammonium salts by alkylation. The availability of these salts thus depends on the accessibility of the corresponding tertiary amines.

Tertiary amines have hitherto essentially been prepared by catalytic hydrogenating alkylation of amine/alcohol or amine/aldehyde mixtures. Typical side reactions are trans-alkylations, which, especially in the case of unsymmetrically substituted amines, lead to product mixtures which can be worked up only with difficulty. In particular, product mixtures are obtained in the reaction of polyalkylene glycol ethers, as the alcohol component, with amines under alkylating hydrogenation conditions as a result of splitting of the ether. It is therefore very difficult to prepare, in good yield, tertiary alkyl- or aryl-polyether-amines having a particular structure, and consequently corresponding quaternary ammonium salts are also not readily accessible.

In contrast, (poly)alkanolamines having free hydroxyl groups and ammonium salts thereof are readily accessible, in particular by oxyalkylation of ammonia or a primary or secondary amine with an alkylene oxide, in which a quaternary ammonium salt, which, like the alkanolamine employed, still contains hydroxyl groups, is obtained with an alkylating agent in a conventional manner. In many fields of use, these quaternized alkanolamines are inferior to the simple polyalkylammonium salts.

There has as yet been no possibility of obtaining good yields of polyether-quaternary salts with blocked end groups by etherifying the hydroxyl groups of these alkanolammonium salts. When prepared from an alcoholate and an alkylating agent, eg. an alkyl halide, under Williamson ether synthesis conditions, the quaternary salts decompose by Hofmann degradation.

I have found that alkylation of an alkanolamine (I) or an alkanolammonium salt (II) with an alkylating agent $R^3X$ (III) or $R^4X$ (IV) in the presence of a phase transfer catalyst under mild conditions gives a quantitative yield of novel substances, namely polyether-quaternary salts (V) with blocked end groups, in accordance with the following equation:

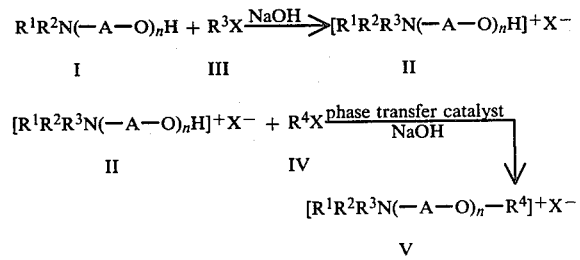

The first reaction can evidently be regarded as N-alkylation and the second as O-alkylation.

$R^1$ and $R^2$ can be identical or different and each is alkyl, cycloalkyl, aryl, aralkyl, alkylaryl or alkoxyalkyl or a (poly)alkylene glycol radical, or $R^1$ and $R^2$, together with the nitrogen atom, can also be a heterocyclic ring, which may contain further hetero-atoms, in which case $R^1$ and $R^2$ together are a divalent alkylene, oxaalkylene or azaalkylene radical, which, depending on availability, may also contain one or more, generally short-chain, alkyl substituents.

If a polyfunctional amine in which one or more substituents $R^1$ or $R^2$ are in turn substituted by a tertiary amino group $-NR^1R^2$ is used as the starting material, the novel quaternary salt can likewise contain several ammonium groups.

In the above formulae, A furthermore is alkylene of 2 to 10 C atoms, X is a substituent of a conventional alkylating agent, in particular a halide, a (metho)sulfate or an (alkyl)aryl-sulfonate, and n is an integer, in particular an integer from 1 to 5.

$R^1$, $R^2$ and $R^3$ can in themselves be any desired shape and size, for example straight-chain or branched. In general, compounds in which these substituents are alkyl of 1 to 20, in particular 2 to 20, carbon atoms, aryl of 6 or 10 carbon atoms, alkylaryl or aralkyl of 7 to 20 carbon atoms, alkoxy(polyoxy)alkyl of 3 to 100 or more carbon atoms or (poly)alkylene glycol groups of 2 to 100 or more carbon atoms are of particular industrial interest.

The alkanolamines can accordingly be reaction products of ammonia, a primary or secondary alkylamine, a polybasic amine or a polyamine and an alkylene oxide, eg. dimethylethanolamine, triethanolamine, triisopropanolamine, butyldiethanolamine, diethylethanolamine, tetrahydroxyethylhexamethylenediamine and (poly)oxyalkylates thereof, and also alkanolamines of a different origin, eg. 3-dimethylaminopropanol, dimethylneopentenolamine, N,N'-dimethylneopentanediamine and oxyalkylates thereof. Suitable alkylene oxides include ethylene oxide, propylene oxide and butylene oxide. Most of the above alkanolamines, and many other such compounds, are commercially available.

Conventional alkylating agents $R^3X$ (III) and $R^4X$ (IV) which can be used are alkyl, (alkyl)aryl, benzyl or 2-alkylene halides, methosulfates, and arylsulfonates, for example benzyl chloride, methyl chloride, cyclohexyl bromide, dimethyl sulfate and methyl p-toluenesulfonate.

In principle, any alkali metal hydroxide or alkaline earth metal hydroxide may be used as the base, but sodium hydroxide solution is preferred, for economic reasons.

Suitable phase transfer catalysts are quaternary ammonium salts, such as are described in the relevant literature (cf. E. V. Dehmlow, Angew. Chem. 86, (1974), 187–196), eg. trialkylbenzylammonium salts and tetraalkylammonium salts. These ammonium salts can be added as catalysts before the reaction, or they can be prepared in situ from a tertiary amine in the course of the alkylation reaction (for example, triethylbenzylammonium chloride can be prepared from triethylamine and benzyl chloride).

The reaction according to the invention sometimes proceeds autocatalytically, ie. the quaternary salt formed catalyzes its own etherification, so that separate addition of a phase transfer catalyst would be superfluous. This situation can always be achieved by a procedure in which part of the reacted mixture is recycled or used as the solvent, especially in the case of continuous operation.

The reaction can be carried out as a one-stage process, but is preferably carried out as a two-stage process. In this case, the first step is quaternization (N-alkylation) of the initially introduced alkanolamine to the alkanolammonium salt with an alkylating agent at from 20° to 160° C., preferably at from 40° to 120° C. The etherification (O-alkylation) under phase transfer catalysis does not take place until the second step, after addition of an alkali (preferably as an aqueous alkali metal hydroxide solution in a concentration of from 10 to 60%), at from 20° to 90° C., in particular from 30° to 60° C. The alkylating agent ($R^3X$) in the first step may in each case differ from that in the second step ($R^4X$). If the same alkylating agent is used in the quaternizing stage as in the etherification stage, a one-stage reaction is also possible, in which case the alkanolamine and the alkali metal hydroxide solution and, where relevant, the foreign phase transfer catalyst are introduced jointly and the above alkylating agent can then be added in one step or at the rate at which it reacts. The quaternizing step can be monitored with the aid of the amine number and, where relevant, the etherification step can be monitored by the liberation of halide, but also by the OH number of a sample of the reaction mixture.

The reaction can be carried out in the mixture per se, or in the presence of a suitable solvent, eg. benzene, toluene, chlorobenzene, carbon tetrachloride, methylene chloride and the like, but preferably in water. It usually proceeds under atmospheric pressure.

The anion X of the alkylating agent can be replaced by any other desired inorganic or organic anion, and halides, sulfates, phosphates, nitrates and carboxylates are preferred.

The reaction mixture is worked up by separating off the alkali metal hydroxide solution, where relevant after dilution with a solvent, eg. isobutanol, isopropanol or another solvent which is immiscible or only slightly miscible with the alkali metal hydroxide solution. Evaporation of the solvent under reduced pressure first gives a crude product which in most cases is pasty. This can be purified further; for example, recrystallization from ethyl acetate or toluene has proved suitable for a large number of products, white, crystalline products of definite melting point being obtained.

The particular advantages of the process described are that the quaternary ammonium salts can be synthesized, starting from an amine or ammonia, in a single reaction chamber, eg. a stirred kettle or a cascade of stirred kettles, under mild reaction conditions, working up of the mixtures is simple, without a distillation step for separating mixtures of the desired products, the synthesis is controlled and gives defined products and not isomer mixtures, and quaternary ammonium salts can be synthesized without the use of trisalkylamines which are not readily accessible.

The resulting polyether-quaternary salts can be used for the purposes conventional for quaternary ammonium salts, for example as textile assistants, cationic surfactants and the like.

The individual substances listed as examples in the Table which follows can all be obtained in accordance with the instructions below.

1.1 equivalents of the alkylating agent are added a little at a time to 1 equivalent of a tertiary alkanolamine and 0.03 equivalent of benzyltriethylammonium chloride at the required quaternization temperature (see Table), and the mixture is stirred until the amine titer is less than 0.1 m equivalent/g. The mixture is then left to cool, (n+1) moles of NaOH, in the form of a 50% strength aqueous solution, are added, with further cooling to 40° C., for n moles of hydroxyl groups to be etherified, and a further n moles of alkylating agent are then added, with vigorous stirring. Stirring is continued at 40° C. for some hours, and if necessary the mixture can be diluted with water for easier stirring. Isobutanol and a sufficient amount of water to dissolve all the solids are then added, with stirring, stirring is continued for half an hour, and the aqueous alkali metal hydroxide solution is decanted off. The remaining mixture is washed with water and, finally, the solvent is distilled off under reduced pressure. If necessary, the resulting pasty crude product can be precipitated by being poured into from 250 to 500 ml of ethyl acetate and, finally, can be filtered off.

| Example No. | Starting materials | Reaction conditions Quaternization Temperature | Subs. stirring time | Yield | Structural formula | Empirical formula | Product Elementary analysis C % | H % | N % | Cl⊖ % | OHZ no. | Melting point (EA) °C. | ¹H—NMR (starter in ppm) |
|---|---|---|---|---|---|---|---|---|---|---|---|---|---|
| 1 | 89.1 g (1 mole) of dimethyl-ethanol-amine 265.9 g (2.1 mole) of benzyl chloride 80 g of NaOH | 100° C. | 12 hours | 281 g | (H₃C)₂N⊕—C₂H₄OCH₂φCl⊖ <br> \|  <br> CH₂ <br> \|  <br> φ | C₁₈H₂₄NOCl | 70.1 (70.7) | 7.8 (7.8) | 4.2 (4.6) | 11.8 (11.6) | 13 (O) | 180 | in CDCl₃ <br> δ=3.3(s,6H,N(CH₃)₂) <br> δ=3.9(s,4H,CH₂—CH₂) <br> δ=4.5(s,2H,φCH₂O) <br> δ=5.1(s,2H,φCH₂—H) <br> δ=7.2–7.8(m,10Hφ) |
| 2 | 117.2 g (1 mole) of diethyl-ethanolamine 265.9 g (2.1 mole) of benzyl chloride 80 g of NaOH | 100° C. | 12 hours | 265 g | (H₅C₂)₂N⊕—C₂H₄OCH₂φCl⊖ <br> \|  <br> CH₂ <br> \|  <br> φ | C₂₀H₂₈NOCl | 71.9 (72.0) | 8.5 (8.4) | 4.2 (4.2) | 10.1 (10.6) | 24 (0) | 116 | in CDCl₃ <br> δ=1.4(t,6H,2CH₃) <br> δ3.2–4.1(m,8H,4CH₂) <br> δ=4.6(s,2H,φ-CH₂O) <br> δ=4.9(s,2H,φOH₂N) <br> δ=7.2–7.7(m,10H,φ) |
| 3 | 131.2 g (1 mole) of 4-(2-hydroxyethyl)morpholine 265.9 g (2.1 mole) of benzyl chloride 80 g of NaOH | 100° C. | 12 hours | 196 g | (morpholinium structure with NC₂H₄OCH₂φCl⊖ and CH₂φ substituent) | C₂₀H₂₆NO₂Cl | 68.7 (69.1) | 7.3 (7.5) | 4.2 (4.0) | 10.1 (10.2) | 8 (0) | 152 | in CDCl₃ <br> δ=3.3–4.5(m,12H,6CH₃) <br> δ=4.6(s,2H,φCH₂O) <br> δ=5.2(s,2H,φCH₂N) <br> δ=7.1–7.8(m,10H,φ) |
| 4 | 119.2 g (1 mole) of N-methyl-diethanolamine | 100° C. | 12 hours | 360 g | H₃CN⊕(C₂H₄OCH₂φ)₂Cl⊖ <br> \|  <br> CH₂ <br> \|  <br> φ | C₂₆H₃₂NO₂Cl | 72.7 (73.3) | 7.4 (7.5) | 3.3 (3.3) | 8.5 (8.3) | 4 (0) | 107 | in CDCl₃ <br> δ=3.2(s,3H,CH₃) <br> δ=3.9(s,8H,2C₂H₄) <br> δ=4.5(s,4H,2φCH₂O) <br> δ=5.1(s,2H,φCH₂N) <br> δ=7.2–7.5(m,15H,φ) |

-continued

| Example No. | Starting materials | Reaction conditions Quaternization Temperature | Subs. stirring time | Yield | Structural formula | Empirical formula | Product Elementary analysis C % | H % | N % | Cl⊖ % | OHZ no. | Melting point (EA) °C. | 1H—NMR (starter in ppm) |
|---|---|---|---|---|---|---|---|---|---|---|---|---|---|
| | 392.5 g (3.1 mole) of benzyl chloride 120 g of NaOH | | | | | | | | | | | | |
| 5 | 287.6 g (1 mole) of N—tridecyldiethanolamine 392.5 g (3.1 mole) of benzyl chloride 120 g of NaOH | 100° C. | 12 hours | 340 g | H$_{27}$C$_{13}$—N⊕H(C$_2$H$_4$OCH$_2$φ)$_2$Cl⊖<br>CH$_2$<br>φ | C$_{38}$H$_{56}$NO$_2$Cl | 76.9 (76.8) | 9.2 (9.4) | 2.3 (2.4) | 5.2 (6.0) | 34 (0) | | |
| 6 | 161.3 g (1 mole) of N—n-butyldiethanolamine 392.5 g (3.1 mole) of benzyl chloride 120 g of NaOH | 100° C. | 24 hours | 450 g | n-H$_9$C$_4$—N⊕(C$_2$H$_4$OCH$_2$φ)$_2$Cl⊖<br>CH$_2$<br>φ | C$_{29}$H$_{38}$NO$_2$Cl | 73.8 (74.4) | 8.4 (8.1) | 2.7 (3.0) | 7.3 (7.6) | 14 (0) | | |
| 7 | 149.2 g (1 mole) of triethanolamine 519.0 g (4.1 mole) of benzyl | 110° C. | 20 hours | 364 g | φCH$_2$—N⊕(C$_2$H$_4$OCH$_2$φ)$_3$Cl⊖ | C$_{34}$H$_{40}$NO$_3$Cl | 74.5 (74.8) | 7.3 (7.3) | 2.8 (2.6) | 6.6 (6.5) | 1 (0) | 109 | in CDCl$_3$<br>δ=3.6–4.1(m,12H,3C$_2$H$_4$)<br>δ=4.5(s,6H,3φCH$_2$O)<br>δ=5.1(s,2H,φCH$_2$N)<br>δ=7.2–7.4(m,20H,φ) |

4,482,713

-continued

| Example No. | Starting materials | Reaction conditions Quaternization Temperature | Subs. stirring time | Yield | Structural formula | Product Empirical formula | Elementary analysis C % | H % | N % | Cl⊖ % | OHZ no. | Melting point (EA) °C. | $^1$H—NMR (starter in ppm) |
|---|---|---|---|---|---|---|---|---|---|---|---|---|---|
| | chloride 160 g of NaOH | | | | | | | | | | | | |
| 8 | 236 g (1 mole) of tetrahydroxy-ethyl-ethylene-diamine 784.9 g (6.2 mole) of benzyl chloride 240 g of NaOH | 110° C. | 20 hours | 712 g | (φCH₂OC₂H₄)HC₂H₄)HC₂H₄H(C₂H₄OCH₂φ)₂<br>⊕ ⊕<br>CH₂ CH₂ 2Cl⊖<br>φ φ | C₅₂H₆₂N₂O₄Cl₂ | 74.0 (73.5) | 7.1 (7.3) | 3.3 (3.3) | | 14 (0) | 129 | in CDCl₃<br>δ=3.5–4.3(m,2OH,10CH₂)<br>δ=4.4(m,2H,4φCH₂O)<br>δ=5.3(s,4H,2φCH₂N)<br>δ=7.2–7.8(m,30H,φ) |
| 9 | 131.1 g of dimethyl-neopenta-nolamine 265.9 g (2.1 mole) of benzyl chloride 80 g of NaOH | 110° C. | 12 hours | 188 g | CH₃<br>(H₃C)₂NCH₂—C—CH₂OCH₂φ<br>⊕ │<br>CH₂ CH₃ Cl⊖<br>φ | C₂₁H₃₀NOCl | 75.5 (75.6) | 8.9 (9.0) | 4.0 (4.2) | 10.0 (10.6) | 20 (O) | 94 | in CDCl₃<br>δ=1.3(s,6H,2CH₃)<br>δ=3.3(s,6H,2N—CH₃)<br>δ3.4(s,2H,O—CH₂)<br>δ=3.8(s,2H,N—CH₂)<br>δ=4.5(s,2H,φ-CH₂O)<br>δ=5.1(s,2H,φ-CH₂N)<br>δ=7.1–7.7(m,10H,φ) |
| 10 | 133 g of N,N—di-methyl-O—hy-droxy-ethyl-ethanol-amine 265.9 g of benzyl chloride 80 g of NaOH | 100° C. | 12 hours | 347 g | (H₃C)₂N(C₂H₄O)₂CH₂φCl⊖<br>⊕ │<br>CH₂<br>φ | C₂₀H₂₈NO₂Cl | 68.5 (68.6) | 8.1 (8.0) | 3.6 (4.0) | 8.4 (10.1) | 4 (0) | | in CDCl₃<br>δ=3.3(s,6H,2CH₃)<br>δ=3.7(Cl,8H,4CH₂)<br>δ=4.5(s,2H,φ-CH₂—O)<br>δ=5.0(s,2H,φ-CH₂—N)<br>δ=7.2–7.7(m,10H,φ) |

4,482,713

-continued

| Example No. | Starting materials | Reaction conditions Quaternization Temperature | Subs. stirring time | Yield | Structural formula | Empirical formula | Product Elementary analysis C % | H % | N % | Cl⊖ % | OHZ no. | Melting point (EA) °C. | $^1$H—NMR (starter in ppm) |
|---|---|---|---|---|---|---|---|---|---|---|---|---|---|
| 11 | 147 g of N,N—dimethyl-O—hydroxyethylisopropanolamine 20 g of NaOH | 100° C. | 12 hours | 319 g | (H₃C₂)N⊕—CH₂—CH₂—CH—OC₂H₄OCH₂φ<br>　　　　　　　　CH₂　CH₃　Cl⊖<br>　　　　　　　　φ | C₂₁H₃₀NO₂Cl | 69.7 (69.3) | 8.4 (8.3) | 3.6 (3.9) | 7.8 (9.8) | 22 (0) | | |
| 12 | 115.2 g of 1-(2-hydroxyethyl)-pyrrolidine 265.9 g of benzyl chloride 80 g of NaOH | 100° C. | 12 hours | 235 g | CH₂CH₂　　NC₂H₄OCH₂φCl⊖<br>　　　　⊕<br>CH₂—CH₂CH₂<br>　　　　φ | C₂₀H₂₆NOCl | 71.9 (72.4) | 7.9 (7.8) | 3.9 (4.2) | 10.4 (10.7) | 12 (0) | 114 | in CDCl₃<br>δ=2.2(m,4H,2CH₂)<br>δ=3.8(m,8H,4CH₂)<br>δ=4.6(s,2H,φ-CH₂O)<br>δ=4.9(s,2H,φCH₂—N)<br>δ=7.2–7.7(m,10H,φ) |
| 13 | 129.2 g of 1-(2-hydroxyethyl)piperidine 265.9 g of benzyl chloride 80 g of NaOH | 100° C. | 12 hours | 389 g | C₂H₄　　NC₂H₄OCH₂φCl⊖<br>　　⊕　CH₂<br>CH₂　C₂H₄—CH₂N<br>　　　φ | C₂₁H₂₈NOCl | 72.5 (72.9) | 8.1 (8.1) | 3.9 (4.1) | 10.1 (10.2) | 18 (0) | 162 | in CDCl₃<br>δ=1.8(m,6H,3CH₂)<br>δ=3.8(m,8H,4CH₂)<br>δ=4.6(s,2H,φ-CH₂—O)<br>δ=5.1(s,2H,φ-CH₂N)<br>δ=7.2–7.8(m,10H,φ) |
| 14 | 270.3 g of N,N—dibutyl-N—(triethylene glycol)-amine 265.9 g of benzyl chloride | 100° C. | 12 hours | 464 g | (H₉C₄)₂N⊕(C₂H₄O)₃CH₂φCl⊖<br>　　　　CH₂<br>　　　　φ | C₂₈H₄₂NO₃Cl | 70.3 (70.7) | 9.1 (8.8) | 2.5 (2.9) | 6.4 (7.5) | 15 (0) | | in CDCl₃<br>δ=0.8–2.1(m,14H,2C₃H₇)<br>δ=3.2(m,4H,2CH₂)<br>δ=3.9(m,12H,6CH₂)<br>δ=4.5(s,2H,φCH₂O)<br>δ=4.9(s,2H,φCH₂N)<br>δ=7.2–7.7(m,10H,φ) |

-continued

| Example No. | Starting materials | Reaction conditions Quaternization Temperature | Subs. stirring time | Yield | Structural formula | Product Empirical formula | Elementary analysis C % | H % | N % | Cl⊖ % | OHZ no. | Melting point (EA) °C. | ¹H—NMR (starter in ppm) |
|---|---|---|---|---|---|---|---|---|---|---|---|---|---|
| | 80 g of NaOH | | | | | | | | | | | | |
| 15 | 175.9 g of pentahydroxy-ethyldi-propylenetri-amine 525.4 g (4.15 mole) of benzyl chloride 120 g of NaOH | 100° C. | 20 hours | 571 g | (φCH₂OC₂H₄)₂N⊕[C₃H₆—N⊕(C₂H₄OCH₂φ)]₂C₂H₄OCH₂φ         CH₂ CH₂         φ   φ   3Cl⊖ | C₇₂H₈₈N₃/₅Cl₃ | 73.1 (73.2) | 7.9 (7.5) | 3.5 (3.6) | 6.4 (0) | 19 | | |
| 16 | 103.2 g of 3-di-methyl-amino-propanol 265 g of benzyl chloride 80 g of NaOH | 100° C. | 12 hours | 252 g | (H₃C)₂N⊕C₃H₆OCH₂φCl⊖      CH₂      φ | C₁₉H₂₆NOCl | 70.9 (71.4) | 8.1 (8.1) | 4.0 (4.4) | 11.4 (11.1) | 19 (0) | 112 | in CDCl₃ δ=2.2(m,2H,CH₂) δ=3.3(s,6H,2CH₃) δ=3.6(m,4H,2CH₂) δ=4.4(s,2H,φCH₂O) δ=4.9(s,2H,φCH₂H) δ=7.1-7.7(m,10H,φ) |
| 17 | 146.3 g of tetrahydroxy-ethyl-hexa-methyl-enedi-amine 392.5 g of benzyl chloride 120 g of NaOH | 110° C. | 24 hours | 412 g | (φCH₂OC₂H₄)₂N⊕C₆H₁₂N⊕(C₂H₄OCH₂φ)₂        CH₂  CH₂        φ    φ  2Cl⊖ | C₅₆H₇₀N₂O₄Cl₂ | 75.2 (75.4) | 8.0 (7.9) | 3.0 (3.1) | 7.8 (8.0) | 18 (0) | 129 | in CDCl δ=1.2(m,4H,2CH₂) δ=1.9(m,4H,2CH₂) δ=3.2-4.2(m,20H,10CH₂) δ=4.5(s,8H,4φCH₂O) δ=4.9(s,4H,2φCH₂N) δ=7.0-7.8(m,30H,φ) |

-continued

| Ex-am-ple No. | Starting materials | Reaction conditions Quatern-ization Temperature | Subs. stir-ring time | Yield | Structural formula | Empirical formula | Product Elementary analysis C % | H % | N % | Cl⊖ % | OHZ no. | Melt-ing point (EA) °C. | ¹H—NMR (starter in ppm) |
|---|---|---|---|---|---|---|---|---|---|---|---|---|---|
| 18 | 138.4 g of heptahy-droxy-ethyl-tetra-propyl-enepent-amine 395.6 g of benzyl chloride 120 g of NaOH | 110° C. | 24 hours | 399 g | (φCH₂OC₂H₄)₂N⊕(C₂H₆N⊕(C₂H₄OCH₂φ)₄]₄C₂H₄OCH₂φ  \|  CH₂ CH₂  \|  φ φ  5Cl⊖ | C₁₁₀H₃₆N₅O₇Cl₅ | 72.6 (72.7) | 7.7 (7.5) | 4.0 (3.9) | 5.4 (5.4) | 16 (0) | | |
| 19 | 191.3 g of triisopro-panol-amine 519.0 g of benzyl chloride 160.0 g of NaOH | 120° C. | 24 hours | 555 g | φCH₂N⊕(CH₂CHOCH₂φ)₃  \|  CH₃  Cl⊖ | C₃₇H₄₆NO₃Cl | 75.2 (75.6) | 7.9 (7.8) | 2.3 (2.4) | 6.2 (6.0) | 10 (0) | 143 | in CDCl₃ δ=1.0(m,9H,3CH₃) δ=3.4(m,6H,3CH₂) δ=4.5(m,6H,3φCH₂O) δ=4.6(s,2H,φCH₂N) δ=5.1(q,3H,3CH) δ=6.9-7.8(m,20H,φ) |
| 20 | 119.2 g of methyldi-ethanol-amine 265.9 g of benzyl chloride 80 g of NaOH | 100° C. | 12 hours | 222 g | C₂H₄OH  \|  H₃C—⊕N—C₂H₄OCH₂φCl⊖  \|  CH₂  \|  φ | C₁₅H₂₆NO₂Cl | 68.5 (68.0) | 7.9 (7.7) | 4.4 (4.2) | 10.8 (10.6) | 176 (167) | | |
| 21 | 103.2 g of dimethyl-isopro-panol-amine 80 g of NaOH | 100° C. | 12 hours | 317 g | (H₃C)₂N⊕—CH₂—CHOCH₂φ  \|  \|  CH₂ CH₃  \|  φ  Cl⊖ | C₁₉H₂₆NOCl | 70.9 (71.4) | 8.0 (8.1) | 4.1 (4.4) | 10.6 (11.1) | 12 (0) | | in CDCl₃ δ=1.9(s,1H,OH) δ=3.2(s,3H,1CH₃) δ=3.4-4.2(m,8H,4CH₂) δ=4.5(s,2H,φ-CH₂O) δ=4.9(s,2H,φ-CH₂N) δ=7.1-7.7(m,10H,φ) |

-continued

| Example No. | Starting materials | Reaction conditions Quaternization Temperature | Subs. stirring time | Yield | Structural formula | Empirical formula | Product Elementary analysis C % | H % | N % | Cl⊖ % | OHZ no. | Melting point (EA) °C. | ¹H—NMR (starter in ppm) |
|---|---|---|---|---|---|---|---|---|---|---|---|---|---|
| 22 | 187.9 g of N—tridecyl—N—N—bis-(O—hydroxy-ethyl-ethanolamine) 196.2 g of benzyl chloride 60 g of NaOH | 110° C. | 24 hours | 313 g | H₂₇C₁₃⊕N(C₂H₄OC₂H₄OCH₂φ)₂Cl⊖<br>\|<br>CH₂<br>\|<br>φ | C₄₂H₆₄NO₄Cl | 74.5 (74.0) | 9.4 (9.4) | 2.0 (2.1) | 4.8 (5.2) | 13 (0) | | |
| 23 | 89.1 g of dimethyl-ethanol-amine 126.1 g of dimethyl-sulfate 126.6 g of benzyl chloride 80 g of NaOH | 60° C. | 12 hours | 288 g | (H₃C)₃⊕NC₂H₄OCH₂φ<br>⊖O₃SOCH₃ | C₁₃H₂₃NSO₅ | 51.3 (51.1) | 7.8 (7.5) | 4.5 (4.6) | 0.2 (0) | 10 (0) | | |
| 24 | 149.2 g (1 mole) of tri-ethanol-amine 313.6 g (4.1 mole) of allyl chloride 160 g of NaOH | 50° C. | 12 hours | 211 g | H₂C=CH—CH₂⊕N(C₂H₄OCH₂CH=CH₂)<br>Cl⊖ | C₁₈H₃₂NO₃Cl | 61.9 (62.5) | 9.5 (9.3) | 3.8 (4.0) | 10.6 (10.3) | 5 (0) | 80 | in CDCl₃<br>δ=3.7-4.2(m,12H,6CH₂)<br>δ=4.3(d,2H,CH₂—N)<br>δ=4.9-6.2(m,12H,CH=CH₂)<br>¹³C—NMR-Spectrum(CDCl₃)<br>δ=60 ppm(3N—CH₂)<br>δ=64 ppm(3O—CH₂—)<br>δ=65 ppm(1N—CH₂)<br>δ=72 ppm(3O—CH₂)<br>δ=118 ppm(3CH₂=)<br>δ=125 ppm(1CH=)<br>δ=130 ppm(1CH₂=)<br>δ=134 ppm(3CH=) |
| 25 | 89.1 g (1 mole) of dimeth- | 45° C. | 12 hours | 142 g | (H₃C)₃⊕NC₂H₄OCH₃<br>J⊖ | C₆H₁₆NOJ | 29.2 (29.4) | 6.2 (6.5) | 5.7 (5.7) | 51.8 (51.8) | 12 | 235 | in CDCl₃<br>δ=3.2(m,9H,N—CH₃)<br>δ=3.5(s,3H,O—CH₃) |

-continued

| Example No. | Starting materials | Reaction conditions Quaternization Temperature | Subs. stirring time | Yield | Structural formula | Empirical formula | Product Elementary analysis C % | H % | N % | Cl⊖ % | OHZ no. | Melting point (EA) °C. | ¹H—NMR (starter in ppm) |
|---|---|---|---|---|---|---|---|---|---|---|---|---|---|
| | ylethanolamine 284 g (2 mole) of methyliodide 80 g of NaOH | | | | | | | | | | | | δ = 3.5–4.2(m,4H,C—CH₃) |
| 26 | 89.1 g (1 mole) of diethylethanolamine 218 g (2 mole) of ethyl bromide 80 g of NaOH | 40° C. | 12 hours | 185 g | $$H_5C_2\overset{CH_3}{\underset{\underset{\oplus}{CH_3}}{N}}-C_2H_4OC_2H_5 Br^\ominus$$ | C₈H₂₀NOBr | 42.0 (42.5) | 8.9 (8.8) | 5.9 (6.2) | 34.9 (35.3) | 7 | | |
| 27 | 89.1 g (1 mole) of methylethanolamine 185.2 g (2 mole) of n-butyl chloride 80 g of NaOH | 90° C. | 40 hours | 158 g | $$H_9C_4\overset{CH_3}{\underset{\underset{\oplus}{CH_3}}{N}}-C_2H_4OC_4H_9\ Cl^\ominus$$ | C₁₂H₂₈NOCl | 60.1 (60.6) | 11.5 (11.8) | 6.0 (5.9) | 14.9 (14.9) | 16 | 112 | in CDCl₃ δ = 1.0(t,6H,C—CH₃) δ = 1.2–22(m,8H,C₂H₄) δ = 3.4(s,6H,N—CH₃) δ = 3.6–39(m,2H,CH₂—O) δ = 3.9(s,4H,NC₂H₄O) |
| 28 | 287.6 g (1 mole) of tridecyldiethanolamine 126 g (1 mole) of di- | 110° C. | 24 hours | 564 g | $$H_{27}C_{13}\overset{\oplus}{N}(C_2H_4OCH_2\phi)_2\\CH_3\\(Cl^\ominus/CH_3OSO_3^\ominus)$$ | C₃₂H₅₂NO₂Cl C₃₅H₅₅NO₆S | 66.7 | 8.7 | 2.4 | 1.4 | 22 | | |

-continued

| Example No. | Starting materials | Reaction conditions Quaternization Temperature | Subs. stirring time | Yield | Structural formula | Empirical formula | Product Elementary analysis C % | H % | N % | Cl⊖ % | OHZ no. | Melting point (EA) °C. | $^1$H—NMR (starter in ppm) |
|---|---|---|---|---|---|---|---|---|---|---|---|---|---|
| | methylsulfate 253 g (2 mole) of benzyl chloride 120 g of NaOH | | | | | | | | | | | | |
| 29 | 187.2 g (1 mole) of phenyl-diethanol-amine 392.5 g (3.1 mole) of benzyl chloride 120 g of NaOH | 110° C. | 24 hours | 445 g | ⊕N(C$_2$H$_4$OCH$_2$φ)$_2$ \| CH$_2$ \| φ   Cl⊖ | C$_{31}$H$_{33}$NO$_2$Cl | 76.3 (76.3) | 7.2 (7.0) | 3.0 (2.9) | 7.3 (7.3) | 25 | | in CDCl$_3$ δ=3.6(s,8H,2C$_2$H$_4$) δ=4.5(s,4H2φCH$_2$O) δ=4.55(s,2H,1φCH$_2$N) δ=6.5–7.5(m,15H,φ) |

I claim:
1. A process for the preparation of quaternary ammonium salts of the formula

$$[R^1R^2R^3N(A\!-\!O)_n\!-\!R^4]^+Z^-,$$

where $R^1$ and $R^2$ are identical or different and each is alkyl, aryl, aralkyl, alkylaryl, alkoxyalkyl or a (poly-)alkylene glycol radical, or $R^1$ and $R^2$, together with the nitrogen atom, are a heterocyclic ring, or one or more substituents $R^1$ or $R^2$ are poly-functional so that the salt contains not less than 2 ammonium group, $R^3$ and $R^4$ are identical or different monovalent radicals of one or more alkylating agents $R^3X$ or $R^4X$, where $R^3$ and $R^4$ are identical or different and each is alkyl, alkenyl or aralk(en)yl and X is an alkylating substituent, A is alkylene of 2 to 10 carbon atoms, n is an integer and Z is either the substituent X or another salt-forming anion or a hydroxyl ion, wherein a tertiary alkanolamine of the formula $$R^1R^2N(\!-\!A\!-\!O)_nH$$

with not less than one hydroxyl group per molecule is treated simultaneously or successively, with an alkylating agent $R^3X$ and, in the presence of a phase transfer catalyst and an alkali metal hydroxide or an alkaline earth metal hydroxide base, an alkylating agent $R^4X$.

2. The process of claim 1, wherein $R^1$, and $R^2$ are alkyl of 1–20 carbons and at least one of $R^3$ and $R^4$ is benzyl.

3. The process of claim 2, wherein both $R^3$ and $R^4$ are benzyl.

4. The process of claim 3, wherein $R^1$ and $R^2$ are methyl.

* * * * *